United States Patent
Suma

(10) Patent No.: US 12,320,091 B1
(45) Date of Patent: Jun. 3, 2025

(54) SUBTERRANEAN WATER BARRIER

(71) Applicant: Nexuma L.L.C., Sunny Isles Beach, FL (US)

(72) Inventor: Alexander B. Suma, Miami, FL (US)

(73) Assignee: Nexuma L.L.C., Sunny Isles Beach, FL (US)

( * ) Notice: Subject to any disclaimer, the term of this patent is extended or adjusted under 35 U.S.C. 154(b) by 0 days.

(21) Appl. No.: 18/767,086

(22) Filed: Jul. 9, 2024

(51) Int. Cl.
  *C12P 7/24* (2006.01)
  *C12P 3/00* (2006.01)
  *E02D 3/12* (2006.01)
  *C12R 1/01* (2006.01)

(52) U.S. Cl.
  CPC ............... *E02D 3/12* (2013.01); *C12P 3/00* (2013.01); *C12P 7/24* (2013.01); *C12R 2001/01* (2021.05)

(58) Field of Classification Search
  CPC ................................ C09K 17/00; E02D 3/12
  See application file for complete search history.

(56) References Cited

U.S. PATENT DOCUMENTS

2025/0026686 A1* 1/2025 Jiang ................. C12N 1/20

OTHER PUBLICATIONS

Bloetscher, F. et al., Adaptation of Florida's Urban Infrastructure to Climate Change, (2017) Chapter 11, http://purl.flvc.org/fsu/fd/FSU_libsubv1_scholarship_submission_1515510253_5d0b606b, 28 pages.
Bloetscher, F. et al., Can Sea Level Rise and Accompanying Saltwater Intrusion Contribute to Catastrophic Building Failures?, Journal of Engineering and Architecture, Jun. 2023, vol. 11, No. 1, pp. 7-23.
Nagireddi, et al., Carbon Dioxide Capture, Utilization, and Sequestration: Current Status, Challenges, and Future Prospects for Global Decarbonization, ACS Engineering, Aug. 4, 2024, pp. 22-48.
Fiaschi, S. and Wdowinski, S., Local Land Subsidence in Miami Beach (FL) and Norfolk (VA) and its Contribution to Flooding Hazard in Coastal Communities Along the U.S. Atlantic Coast, Ocean and Coastal Management 187 (2020), 9 pages.
Fish, J. and Stewart, M., Hydrogeology of the Surficial Aquifer System, Dade County, Florida, U.S. Geological Survey, Water-Resources Investigations Report 90-4108, Prepared in cooperation with the South Florida Water Management District, 1991, 62 pages.
Harris, P. and Purkis, S., Impact of Facies and Diagenetic Variability on Permeability and Fluid Flow in an Oolitic Grainstone—Pleistocene Miami Oolite, The Depositional Record, 2020; 6:459-470.
Wdowinski, S. et al., Increasing Flooding Hazard in Coastal Communities Due to Rising Sea Level: Case Study of Miami Beach, Florida, Elsevier, Ocean & Coastal Management 126 (2016) 1-8.
Luo, Y. et al., Microscopic Pore Structural Characteristics and Grout Diffusion Law of Carl Reef Limestone, Springer, Marine Geophysical Research (2023) 44:14.
Miami-Dade Back Bay Coastal Storm Risk Management Feasibility Study, Draft Integrated Feasibility Report and Environmental Assessment, Apr. 2024, 222 pages.
Prinos, S. et al., Origins and Delineation of Saltwater Intrusion in the Biscayne Aquifer and Changes in the Distribution of Saltwater in Miami-Date County, Florida, Scientific Investigations Report 2014—5025, 116 pages.
Purkis, S. and Harris, P., Quantitative Interrogation of a Fossilized Carbonate Sand Body—The Pleistocene Miami Oolite of South Florida, Sedimentology (2017) 64, 1439-1464.
Matter, J. et al., Rapid Carbon Mineralization for Permanent Disposal of Anthropogenic Carbon Dioxide Emissions, Science, Jun. 10, 2016, vol. 352 Issue 6291, 5 pages.
University of Miami, Seahive, Idea Project NCHRP-213: Seahive—Sustainable Estuarine and Marine Revetment, PI: Landolf Rhode-Barbarigos, UM CAE, https://www.coe.miami.edu/research/seahive, 2 pages.
Seyyedi, M. et al., Pore Structure Changes Occur During CO2 Injection into Carbonate Reservoirs; Scientific Reports, (2020) 10:3624, 14 pages.

* cited by examiner

*Primary Examiner* — Tekchand Saidha
(74) *Attorney, Agent, or Firm* — Leech Tishman Fuscaldo & Lampl, LLC

(57) ABSTRACT

A water barrier inhibits flow of water through water permeable subsoil. The water barrier includes a mixture of bacteria such as *Sporosarcina pasteurii* that when combined with water and salt reacts with $CO_2$ to build limestone. The water barrier is created by providing a mixture that can fill voids in a water permeable subsoil and introducing the mixture into the water permeable subsoil to fill voids. The mixture is introduced by creating a passage through the water permeable subsoil layer and pumping the mixture into the passage.

22 Claims, 8 Drawing Sheets

SUBTERRANEAN WATER BARRIER

CROSS-REFERENCE TO RELATED APPLICATION n/a.

FIELD

The present technology relates to flood prevention and more particularly to a method and material for creating a subterranean water barrier.

BACKGROUND

Climate change has a devastating effect on coastal cities due to the related rising sea levels. Current predictions estimate a temperature rise of 1.5 degree Celsius in a "minimum" scenario with an estimated sea level rise of 8-20 inches by 2100 and up to 4 degrees Celsius resulting in "maximum" scenario with about 47 inches of sea level rise. In an exemplary costal area, Miami-Dade County Florida, the "minimum" scenario already has an estimated potential for economic damage of 3.5 trillion dollars. When looked at in more limited examples, such as Fisher Island next to Miami Beach, 800 apartments with an average value in 2024 of 4.4 million dollars per unit for a total of 3.52 billion dollars of in total that may be lost due to rising sea levels without some type of intervention.

Known proposals emphasize defense from the direct sea level rise and wave action at the coast where water meets land or a short distance out into the sea. For example, concrete obstructions, such as seawalls, newly grown coral reefs, and artificial barrier islands protect against wave action at the coastline. Increasing the height of sea walls together, street and sewer pumping, and improved drainage systems in urban areas also protect against wave action and mitigates inland flooding. This is represented in FIG. 1 where a water table 10 is shown below the surface of the soil 12 and occasional flood water 14 rises above the surface of the soil. Pumps 16 and drains remove the flood water from above the surface of the soil. While these approaches can be effective in dealing with coastal erosion, and flooding caused by rain, waves, and storms, they do not address inland and coastal flooding from below as water rises through permeable subsoil, such as coral limestone, which literally undermines the effectiveness of the other solutions.

Referring to FIG. 2, a body of water 18, such as a sea, inlet, bay, ocean, lake or river, is shown at a level 20 that is elevated. Without mitigation, salt water 22, shown by arrows, has penetrated the subsoil 24 and perhaps a freshwater aquifer, and the freshwater is salinized. The saltwater flows through and around steel reinforced concrete foundations 26 of large buildings 28 corroding them over time and placing the buildings at severe risk of settling or collapsing. Even when technically possible, the cost of reinforcing or replacing the building foundation in whole or in part is prohibitive. Inland flood water has nowhere to drain unless the surface of the soil is well above sea level, which it is not in many coastal areas. Erecting sea walls no matter how high is futile in combating subsoil water infiltration. The volume of the water is so great that ordinary drainage time can be greatly extended, evaporative drying time can be excessive, and pumping costs become prohibitive even if there is a place to pump the water; and often, there is nowhere to pump the water.

Constant or even periodic flooding causes staggering damage to roads, utilities, and buildings. Vegetation, wildlife, and the entire ecosystem are severely and adversely impacted by the salinization of fresh water or otherwise non-adapted areas. Abandoning the buildings and relocating inhabitants to higher ground inland seems to be the only choice and is presently being contemplated by regional planners. For example, Miami-Dade County has suggested that a managed retreat that accepts the loss of land and damages may be required, wherein about ⅓ of the local population is relocated.

SUMMARY

The present invention confronts the challenges of rising sea level and water table elevation in areas, inland and costal, with water permeable subsoil.

A water barrier inhibits flow of water through water permeable subsoil. The water barrier includes a mixture of bacteria such as *Sporosarcina pasteurii*. When combined with water and salt, the bacteria reacts with $CO_2$ to build limestone. The water barrier is created by providing a mixture that can fill voids in a water permeable subsoil and introducing the mixture into the water permeable subsoil to fill voids. The mixture is introduced by introducing the mixture directly into the soil and a natural passages, spaces, voids through the soil, or creating a passage through the water permeable subsoil layer and pumping the mixture into the passage, and/or using pipes to inject the mixture into selected locations.

The mixture can be pumped into the passage under pressure using pressurized $CO_2$ to cause the mixture under pressure to move outwardly from the passage more than three feet. The mixture can include bacteria that react with $CO_2$ or $O_2$ to form limestone to fill voids in the water permeable subsoil, as well as a polymer, bentonite and/or a mixture with the characteristics of a hydrogel.

An acid can be introduced into the water permeable subsoil prior to introducing the mixture into the water permeable subsoil to create or modify voids in the subsoil. The passage can be same passage through which the mixture is introduced or a separate passage.

Adjacent water barriers can join, merge or overlap to provide a single barrier disposed between a body of water and an inland area and/or one or more buildings can be encircled.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
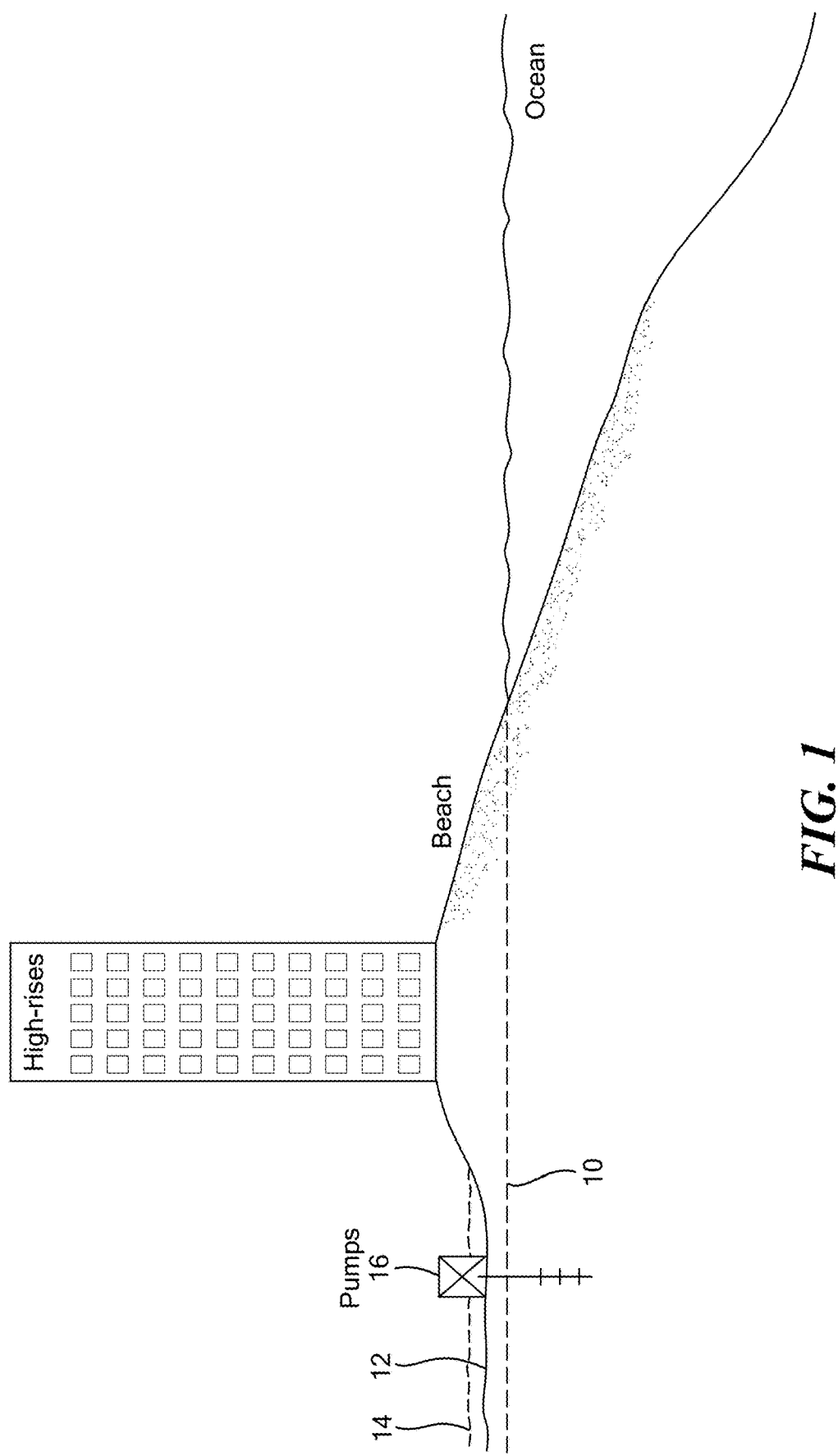
FIG. 1 illustrates an exemplary water table in a costal environment with porous subsoil.
Figure 2:
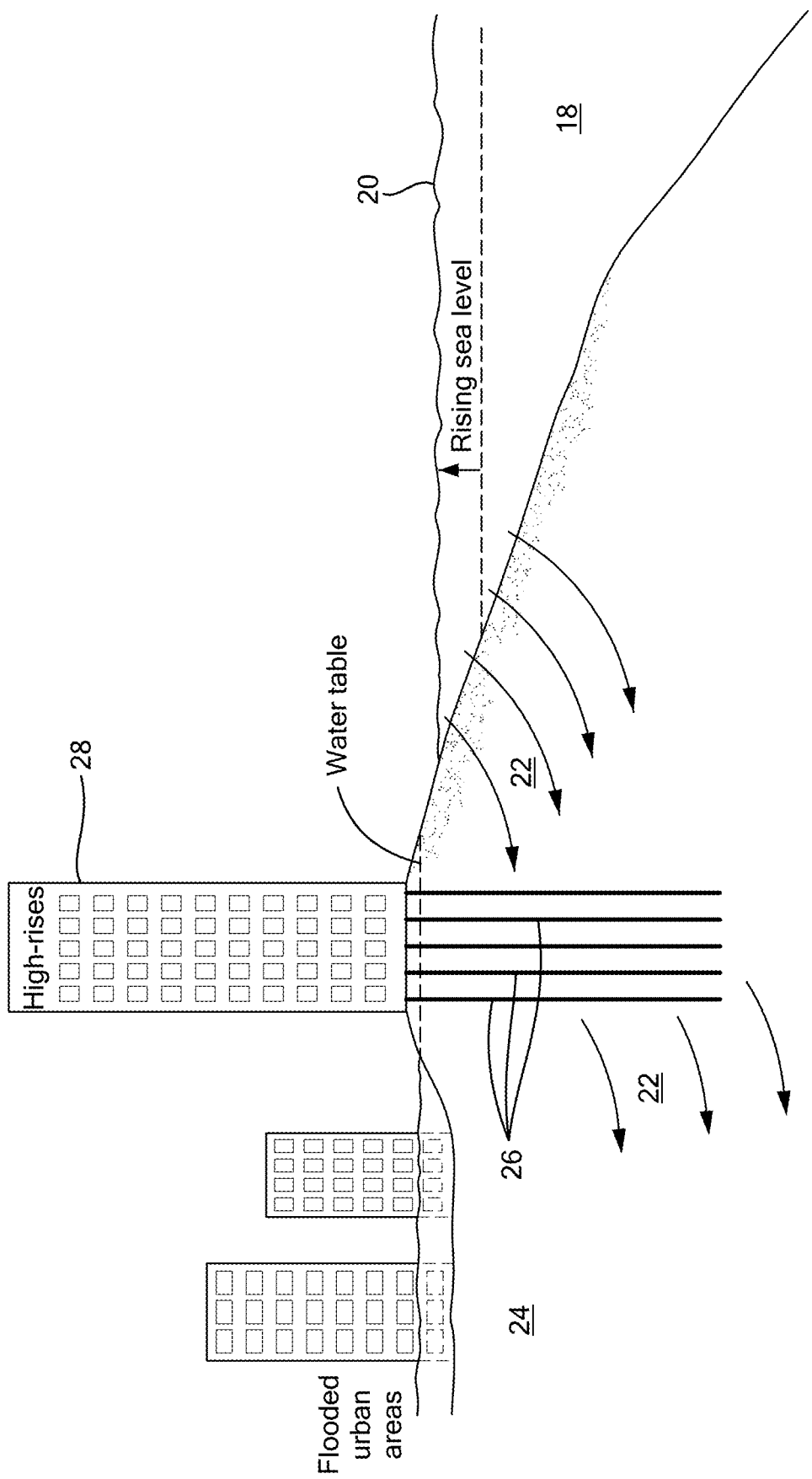
FIG. 2 shows the effect of sea level rise and flooding in the environment of FIG. 1.
Figure 3:
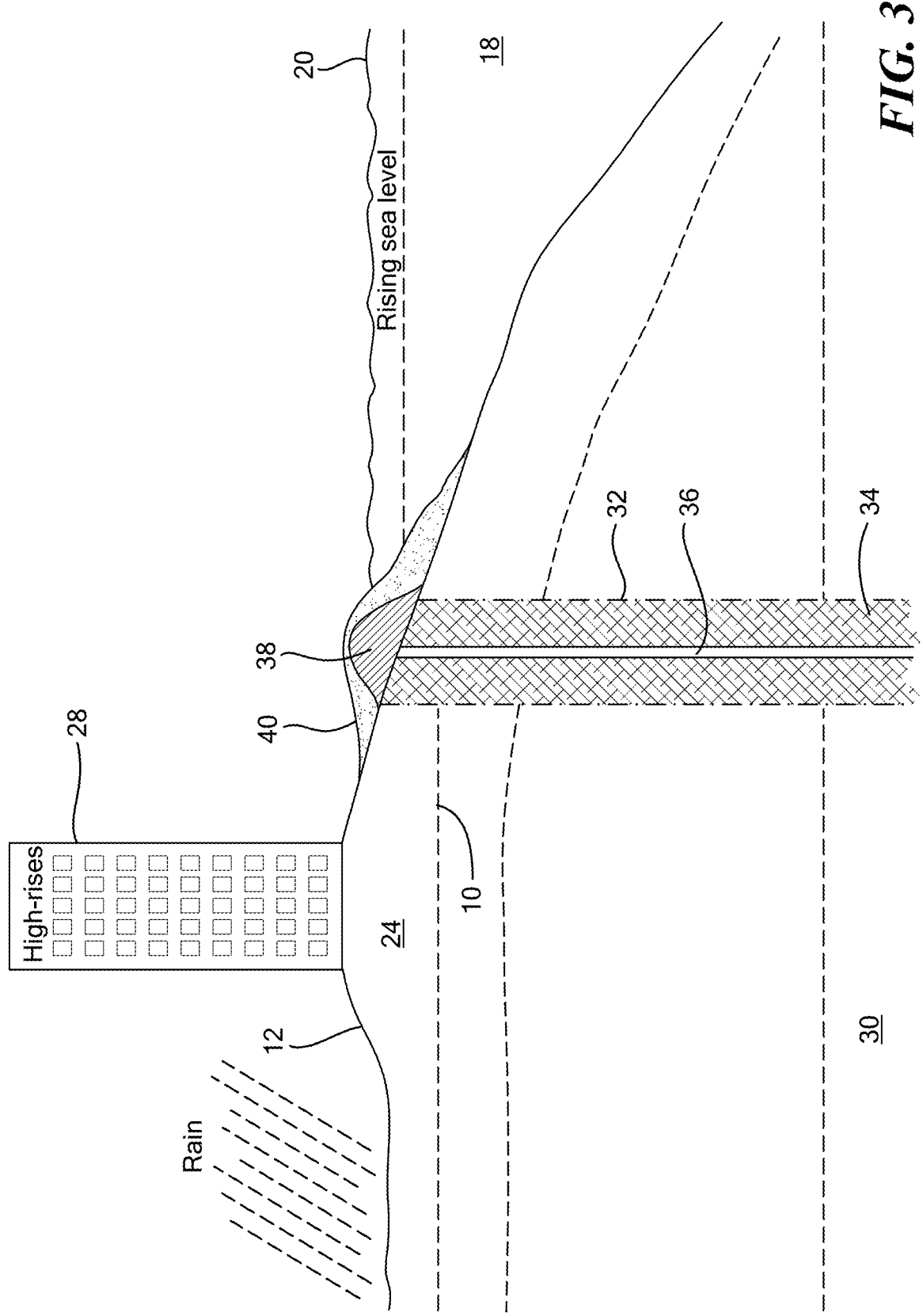
FIG. 3 illustrates an aspect of the present invention, namely a subsoil water barrier that can mitigate the effect of the sea level rise and flooding of FIG. 2.

The present invention provides a method and apparatus for creating a barrier to mitigate the effects of sea level rise and inland flooding. FIG. 3 illustrates a cut-away, side view of a barrier in accordance with the invention. The barrier is particularly well suited for geographic areas with permeable subsoils such as coral and limestone. Florida, for example, has both permeable and non-permeable subsoil throughout the state.

As shown in FIG. 3, a geographic area is shown with a soil surface layer 12, a water permeable subsoil layer 24 below the soil surface layer, and a water impermeable subsoil layer 30 below the water permeable subsoil layer. Florida's soil, for example, can be generally characterized as a series of layers from top to bottom, beginning with a 3-foot layer of dirt, beneath with lies about 30 feet of open, highly porous coral limestone, beneath which lies coral limestone to a depth of 2-3 miles that become progressively less permeable as depth increases. This dirt and limestone layers are generally permeable up to about a 150-foot depth. Below that, the pressure from the depth densifies the limestone and it becomes as good as water impermeable. However, there can be considerable variation from location to location and site investigation with sonar, radar and seismic geo-mapping will aid in characterizing water permeability.

A barrier 32 of non-porous material 34 is shown that extends from proximate the soil surface 12 to a point below the soil surface where the soil is less permeable 24. In some locations the point below the soil surface is a subsoil layer that is substantially or completely water impermeable 30. The depth of the barrier can be modified depending upon the depth where an impermeable subsoil layer begins or where water permeability is reduced enough to reduce flooding from below. In some locations the barrier extends to or below the level of the water impermeable subsoil level so that water cannot flow or infiltrate below the barrier. As described in more detail below, an injection "needle" or pipe 36 for delivery of a sealing mixture that becomes the non-porous material 34 is shown within the barrier 32.

Once the barrier has been created, water from a body of water 18 such as an ocean, lake or river does not pass under the barrier that is formed to protect a specific structure or a region, or it does so at a rate that can be managed with supplemental remediation like pumping. As described in more detail below, any water that falls or flows from the surface "behind" the barrier 32, or flows under the barrier at a reduced rate, can be more readily mitigated, due to a much lower volume, with pumps to maintain a selected, controlled, water table level 10' that will not damage structures or flood the surface of the soil. To provide more protection from rising sea level and wave action, a cap 38, wall, dike, levee, hill or berm (hereinafter a "cap") can be created above the barrier to extend the barrier above sea level to act as a supplemental water barrier. Sand 40 can be placed above the cap to form a new beach that can be planted with appropriate vegetation such as grasses and mangroves to inhibit sand erosion and improve aesthetics. Alternatively, if the barrier is formed offshore, the cap may be under the water, and it can include a supplemental water or wave barrier that extends upwards under the water to act as a wave break like a reef, and perhaps above the level of the water like a seawall.

Figure 4:
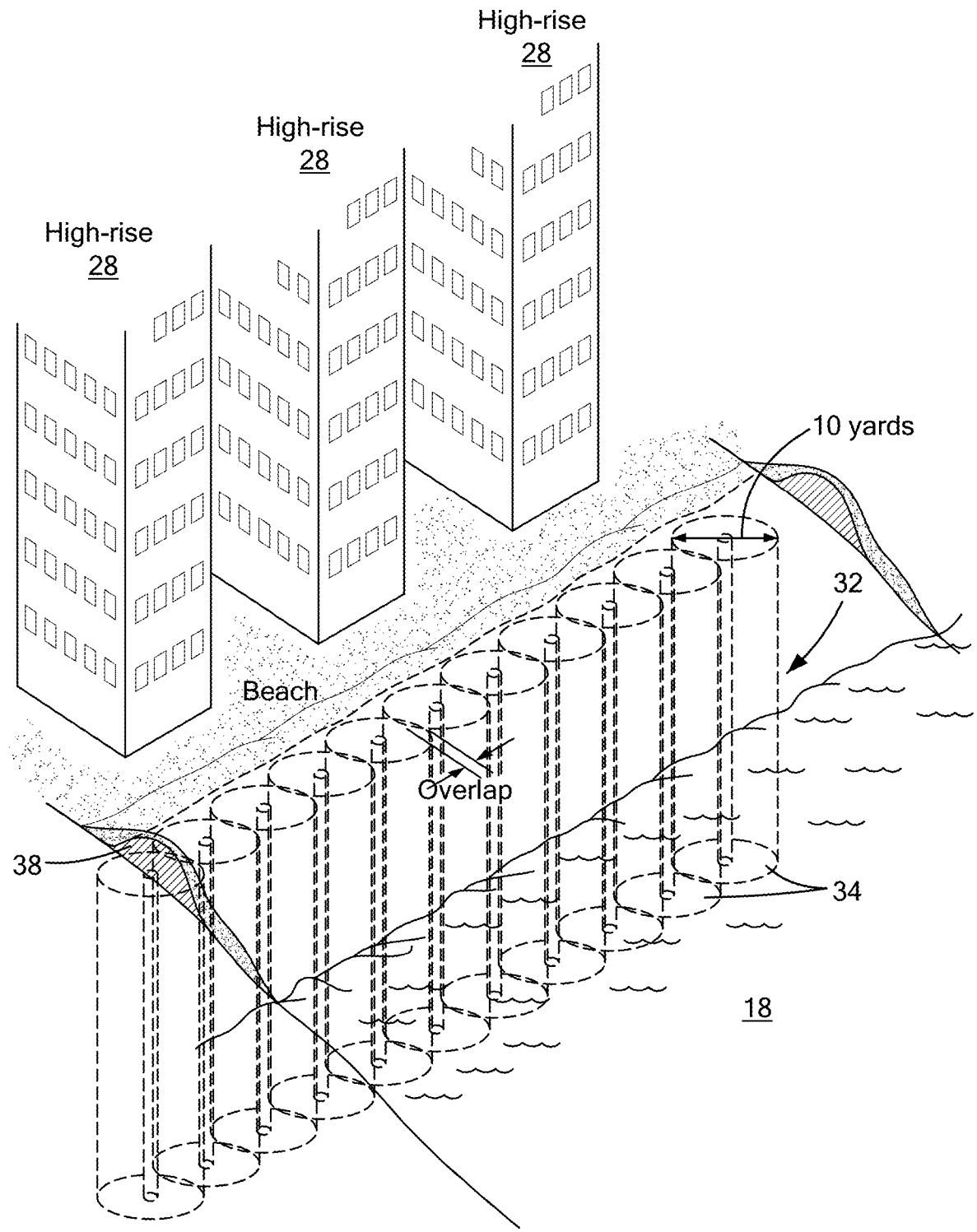
FIG. 4 shows the barrier of FIG. 3 from a different angle to illustrate protection of a large costal region.

FIG. 4 shows the barrier 32 of FIG. 3 from a different angle to illustrate protection of a large costal region. In this view, the barrier 32 is shown as several adjacent elements formed side by side or overlapping so that they abut, join, or comingle to form a unitary barrier. The barrier elements can be substantially vertical as shown, angled or somewhat irregular. The barrier is formed between a body of water, such as the ocean 18, or a protected freshwater body such as the Florida Everglades, and structures inland, such as expensive high-rise buildings 28. The barrier 32 can extend for miles and miles as desired, or it can be limited to a specific area. Further, while shown in a large linear configuration along the beach or coast, the barrier can have a curved, angled, or irregular shape as required by the shape of the coastline or other topographical considerations. Additionally, the barrier can surround or encircle specific areas or buildings to provide "spot" protection.

Figure 5:
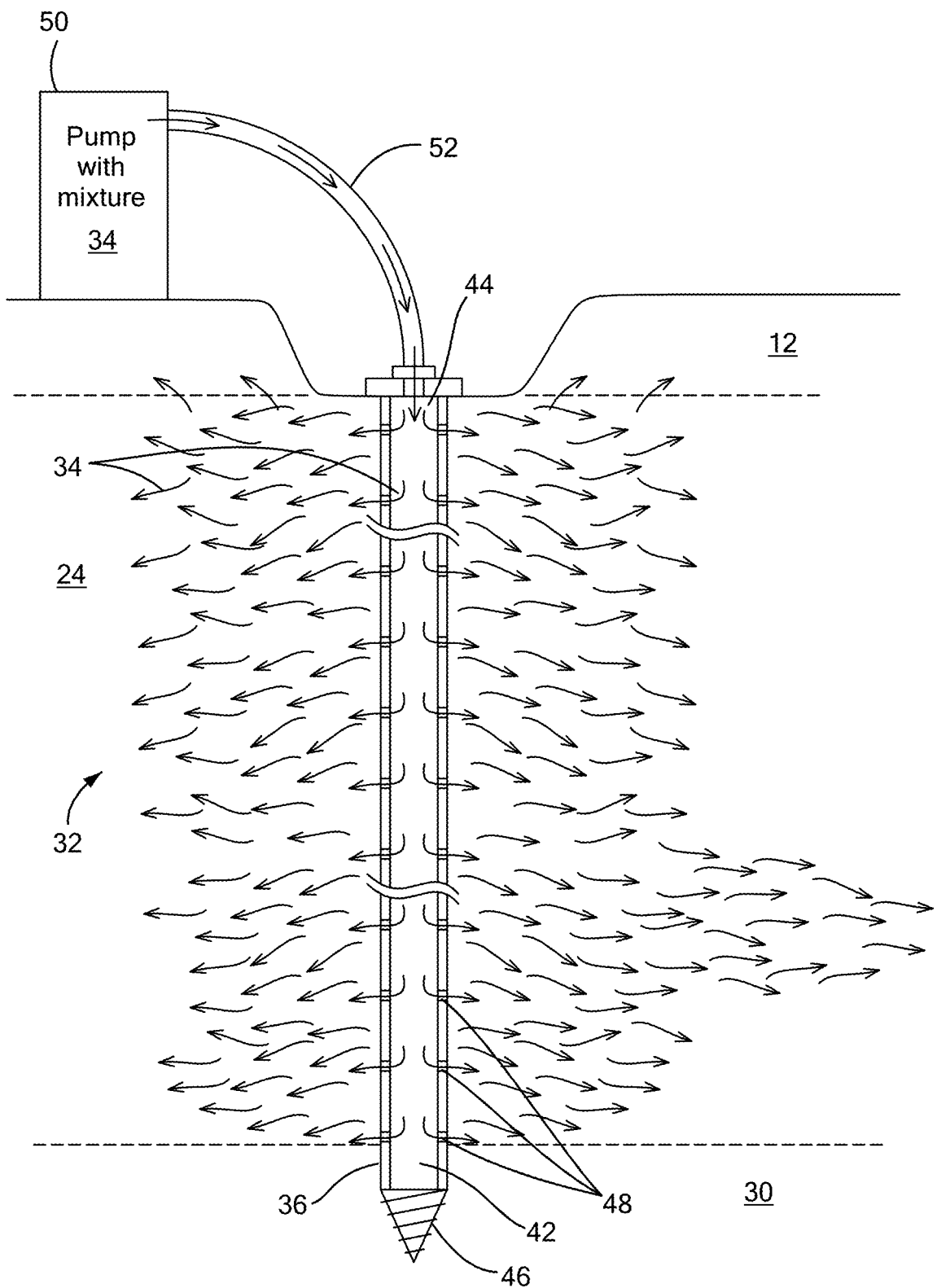
FIG. 5 provides detail of the method of creating the barrier of FIG. 3.

FIG. 5 illustrates an exemplary method wherein the permeability of non-densified dirt/soil/sand/gravel/rock and/or limestone soil or layers 24 is changed by flowing or pumping a sealing mixture or material 34 into subsurface areas. While a passage or hole can be drilled and a sealing material injection device can be placed into the passage or hole, after which a sealing material is flowed or pumped into the passage or hole, in an exemplary method, the drilling and excavating is very minimal in that the device used to deliver the sealing material is like a large "needle," pipe or bit 36 that can be pressed, pounded or screwed into the soil, thereby creating a passage for delivery of sealing material 34, without an additional step of creating a separate bore (hole) and then removing soil and the boring tool from the bore. The pipe 36 can be withdrawn after sealing material 34 is introduced or injected, or it can be left in place for convenience or as a structural reinforcing element for the barrier. The pipe 36 shown includes a hollow portion or lumen 42 extending from a first end 44 to a second end 46 though which sealing material can flow, as well as optional apertures 48 at one or more points along the length of the pipe so that sealing material 34 (represented by arrows) can flow from the lumen 42 to points exterior to the pipe (e.g., into the soil 24).

One or more pumps 50 in communication with supplies of sealing material 34, $CO_2$, acid or other material to aid in sealing, are shown in communication with the lumen of the pipe by a hose 52. The outward flow of the sealing material from the lumen through the apertures and into the soil is shown by the directional head of the arrows. Depending upon the soil conditions, the viscosity of the sealing material, and the delivery pressure of the sealing material, the sealing material can move outward from the second end of the pipe and/or one or more apertures. The mixture or sealing material can flow, migrate, or be pushed a few feet or many yards (e.g., 30 feet or more) away from the pipe or passage to create an infused area of soil that can be 60 or more feet in diameter. Multiple pipes can be used to deliver sealing material at the same time, wherein the pipes are spaced apart a distance that allows the sealing material from adjacent pipes to merge to provide a contiguous barrier and the pipes can be placed hundreds of feet subsurface as required. This technique allows for non-linear barrier formation as required by topography, structures, and subsoil conditions. Additionally, an acid can be introduced into the water permeable subsoil prior to introducing the mixture/sealing material into the water permeable subsoil. The acid can increase void or pore size to allow for more intrusion of the mixture into the subsoil and/or to increase the ratio of mixture to subsoil. Similarly, $CO_2$ can be infused or pumped into the passage and subsoil before or after introduction of the sealing material 34, in addition to during introduction or as a pressurizing force.

The sealing material has sufficient viscosity to flow into pores, gaps, and voids in non-densified limestone, and between grains of sand, rocks and dirt either existing or modified by acid. Once the pores, gaps and voids are filled and the sealing material cures or hardens it creates a water impenetrable structure. Because the non-densified limestone is porous and the mixture is viscous, the mixture flows outward from the hole before it solidifies over its intended diameter. In an exemplary method, the sealing material is a mixture of water and bentonite that is injected into the hole using pressurized $CO_2$. This supplemental pressurization aids in forcing the sealing material outward from the hole and $CO_2$ does not react with water or bentonite. More details about sealing materials are provided below.

Figure 6:
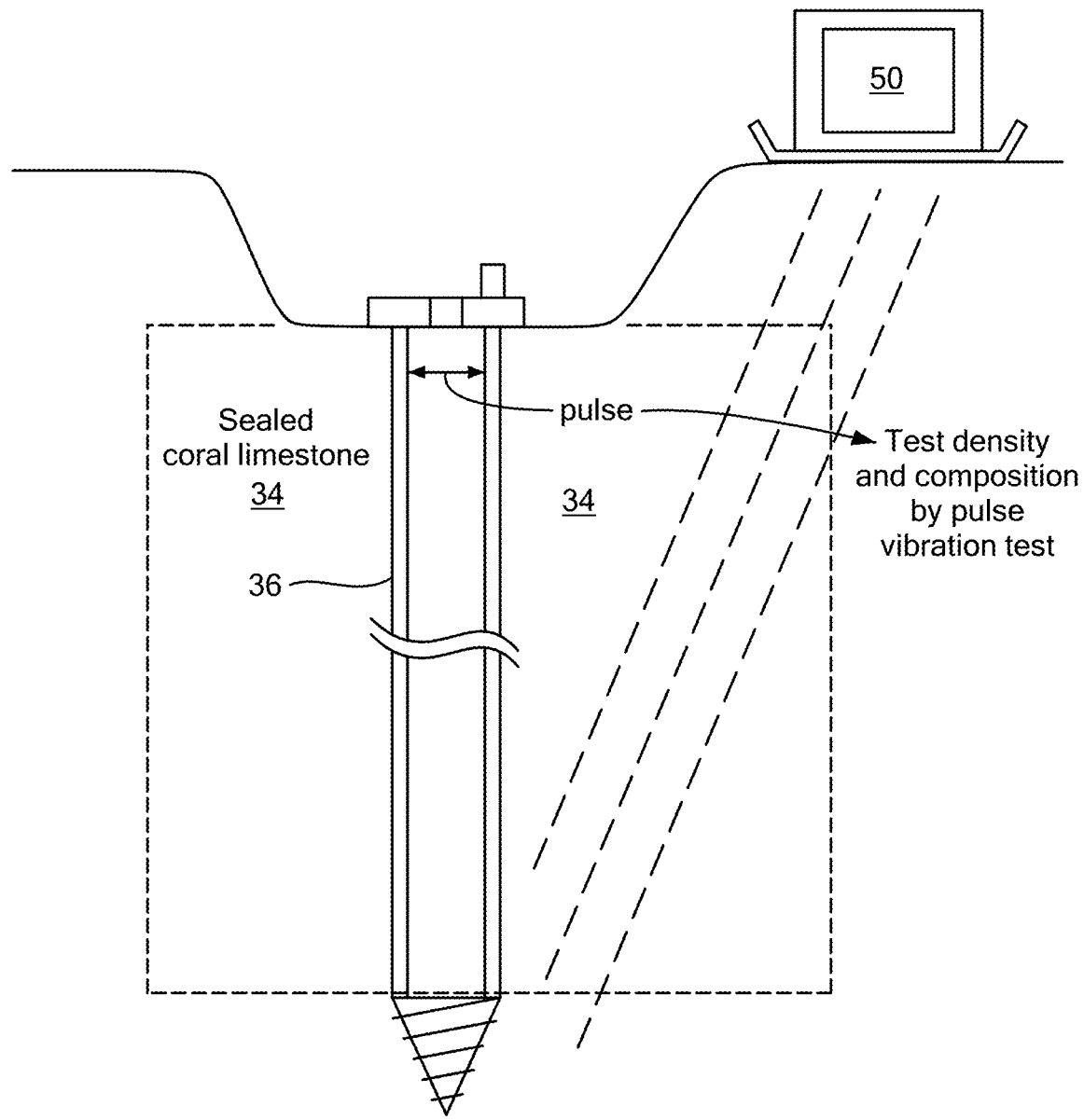
FIG. 6 shows an exemplary apparatus and method of evaluating the barrier of FIG. 3.

Referring now to FIG. 6, an exemplary apparatus and method of evaluating the barrier is depicted. Prior to placement of the injection pipe 36, or after placement, a sonar or seismic device 50 can be used to evaluate the subsurface environment. Density and composition of the subsurface can be evaluated using pulse vibration techniques and/or localized core drilling. This evaluation is used to determine the composition and viscosity of the sealing material that will be introduced into the hole. Similarly, once the sealing material has been introduced into the hole and subsurface layer, the sonar can be used to evaluate the penetration distance from the hole and the sealing of voids. Inadequate penetration can indicate the need for more pressurization, decreasing the viscosity of the sealing material, applying more $CO_2$ and/or nutrition to accelerate the limestone formation process, and/or spot remediation with an additional structure.

Figure 7:
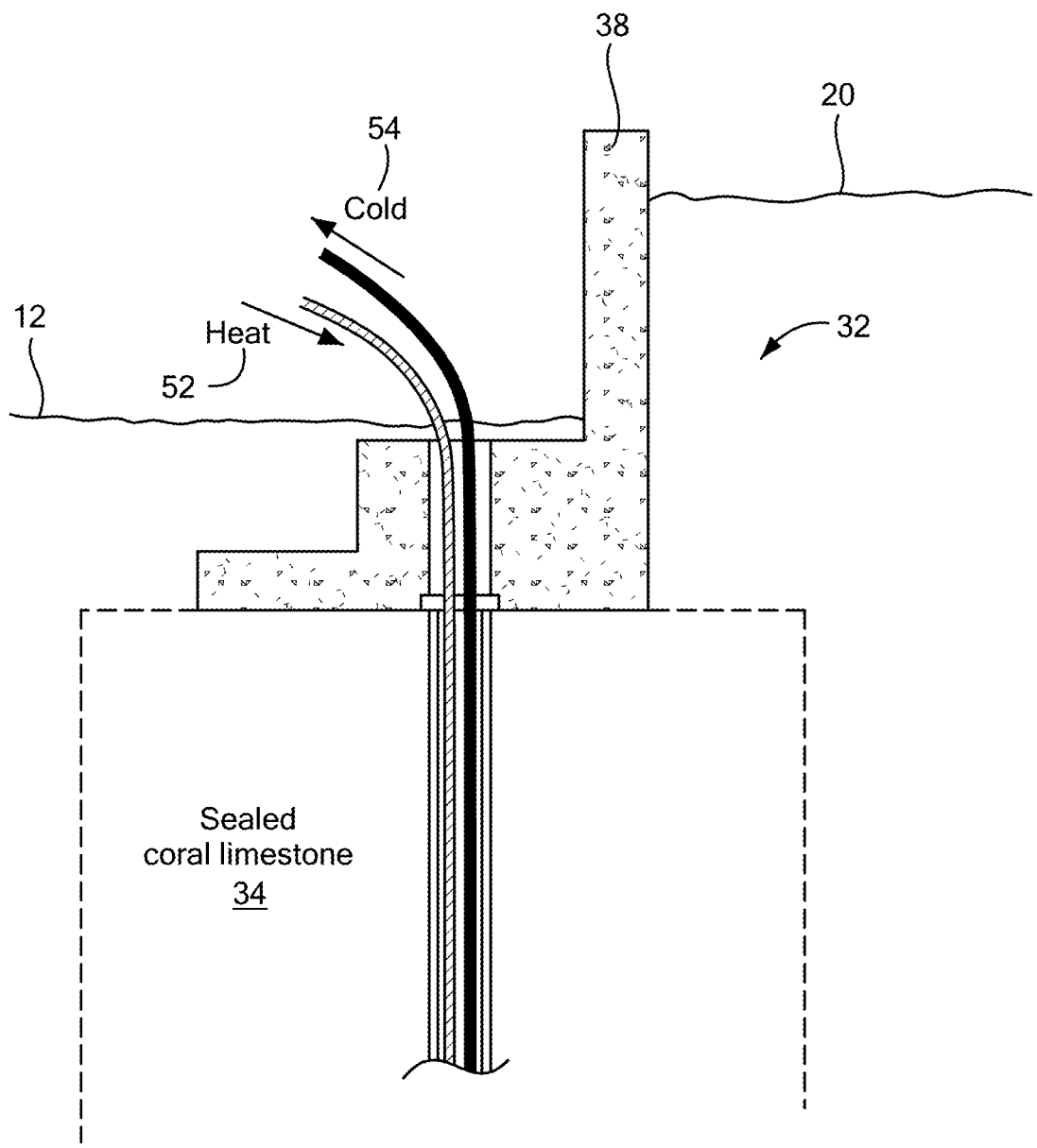
FIG. 7 illustrates an exemplary barrier of the invention that includes a heat exchanger.

Additionally, as shown in FIG. 7, an exemplary barrier 32 of the invention can include tubing 52 and 54 that runs from the surface to a point below the surface to function as a heat exchanger. The underground environment at modest depth such as 100-200 feet is usually warmer or cooler than at the surface. Even a modest temperature differential can allow for low-cost, renewable, geothermal heating or cooling of local buildings. A cover for the hole and top of the barrier can be provided as a cover or cap 38. The cap can be flat, rounded, or be another structure such as a seawall that is shown as part of the barrier 32.

Figure 8:
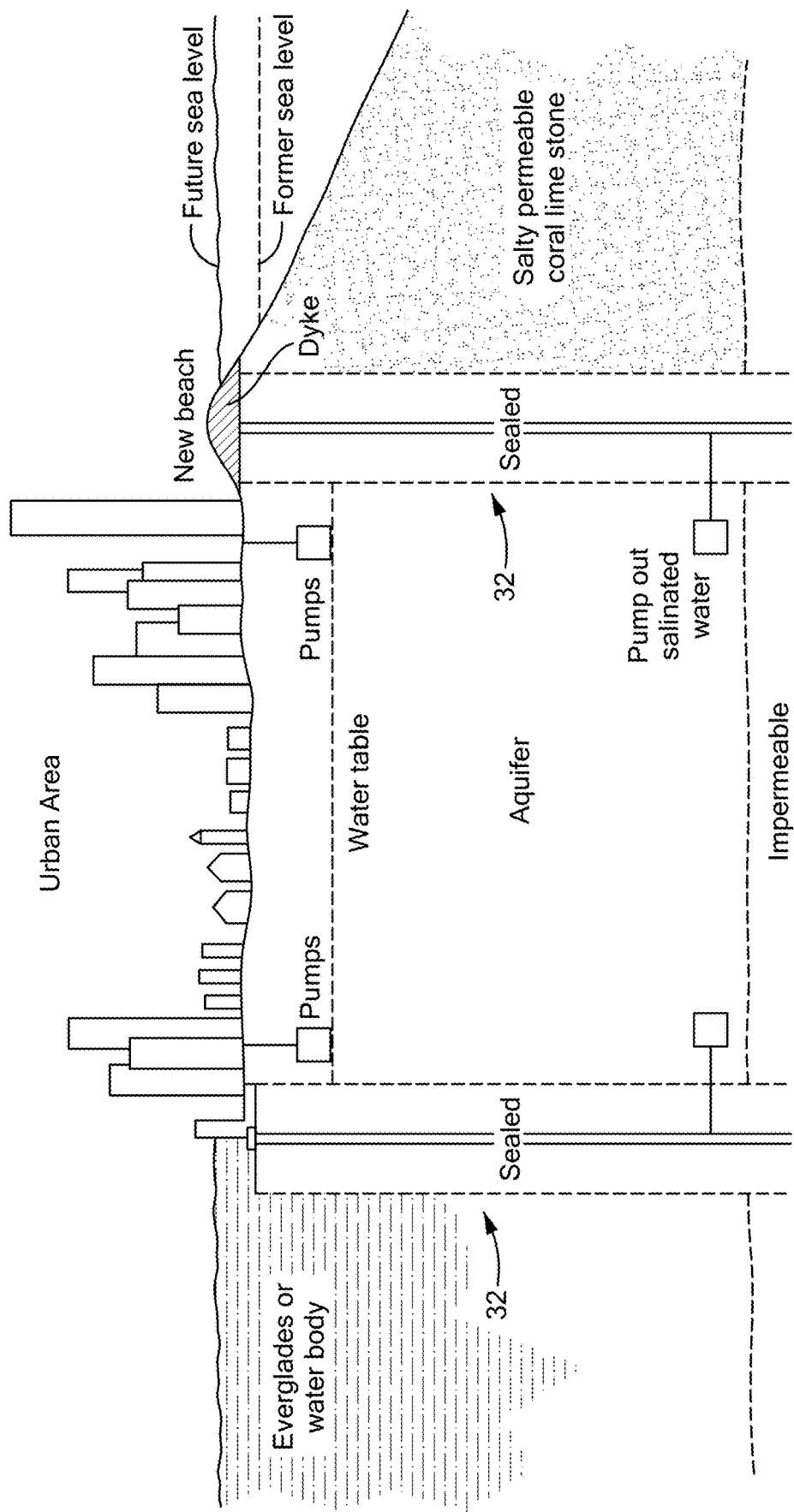
FIG. 8 depicts an urban area near inland and ocean water that is protected from flooding and sea level rise by the present invention.

Thus, as shown in FIG. 8, by providing barriers 32 at selected distances along the coastline, a line of impermeable underground structures creates an underground barrier wall protecting an urban area against bottom-up flooding. Even if the barrier is not impermeable, but rather a flow inhibitor, bottom-up flooding is prevented or reduced and traditional solutions like dikes, sea walls, levies, and other surface or ocean-based measure mentioned above can become more effective. The water table in urban areas can be controlled using pumps while the land area can be retained, real estate protected, and economic loss prevented.

Turning now to the sealing mixture 34, as noted above, the mixture can include water and bentonite. Pressurized $CO_2$ pushes the mixture into voids and distributes it through the soil. As an added environmental benefit, if $CO_2$ is drawn, scavenged or collected from the atmosphere, the $CO_2$ can be sequestered underground to help reduce climate change. In an exemplary formulation, the mixture is heavier than sea water to avoid $CO_2$ leakage before bonding.

An exemplary sealing material includes Microbially Induced Calcite Precipitation (MICP), a biogeochemical process to precipitate calcium carbonate, which can fill and seal pores in limestone leading to impermeability of the soil, sand, rock and gravel. Limestone formation via microbial-induced calcite precipitation (MICP) can be provided with a mixture of the following. Microbes/Bacteria: *Sporosarcina pasteurii* produces the enzyme urease. This enzyme catalyzes the hydrolysis of urea into ammonia and carbon dioxide. Nutrient medium: urea ($CO(NH_2)$). This is the primary substrate that the bacteria use to produce carbonate ions ($CO_3^{2-}$). Calcium Source: commonly calcium chloride ($CaCl_2$)) is used to provide calcium ions ($Ca^{2+}$) which combine with carbonate ions to form calcium carbonate ($CaCO_3$), the main component of limestone. Other Nutrients: the medium also needs to supply other essential nutrients for bacterial growth such as peptone, yeast extract, and possibly sodium chloride (NaCl) to maintain osmotic balance. Carbon Dioxide ($CO_2$): carbon dioxide is involved in the overall reaction and may be a product of the urea hydrolysis process. Additional $CO_2$ is supplied to enhance the precipitation process. Water ($H_2O$): water is necessary as the reaction medium. It facilitates the movement of ions and the growth of bacteria. Salt (NaCl): sodium chloride is added to maintain the osmotic pressure in the bacterial growth medium. The mixture or sealing material can further include microbes that react with $O_2$ to form limestone, and as well as a polymer, a hydrogel, and/or bentonite as noted above. In the event that large voids or pockets need to be filled or solidified, a hydrogel or material that acts like a hydrogel can be used.

In an exemplary method, a measurement of how much salt is present at certain depths in the permeable soil is made to understand how much salt should be included in the mixture. The reaction to solid state can be accelerated by optimizing bacterial growth conditions such as maintaining temperature in a range of around 25-30° C. for *Sporosarcina pasteurii*; pH level ranging from 7.5-9; ensuring oxygen availability as $O_2$ aeration is essential for aerobic bacteria like *Sporosarcina pasteurii* to thrive and perform urea hydrolysis efficiently; and increasing the concentration of urea in the nutrient medium to provide more substrate for urease activity, resulting in higher carbonate ion production. However, extremely high concentrations may inhibit bacterial activity, so a balance is necessary. Higher concentrations of calcium ions (e.g., from calcium chloride) can enhance the availability of calcium for precipitation with carbonate ions. Adding nutrients such as peptone, yeast extract, and other growth-promoting substances can support bacterial growth and activity. Ensuring an ample supply of essential nutrients accelerates the overall process.

The addition of magnesium ions ($Mg^{2+}$) can enhance calcite nucleation and growth. Ammonium Chloride ($NH_4Cl$) can act as a buffering agent, maintaining pH levels conducive to bacterial activity and calcite precipitation. Underground, the pH level is generally similar to salt water. Elevated levels of $CO_2$ can enhance carbonate ion production, accelerating the precipitation process. This can be achieved by direct injection of $CO_2$ or using a $CO_2$-rich environment. Ensuring proper mixing and agitation of the medium can help maintain uniform distribution of bacteria, nutrients, and reactants, leading to more consistent and rapid calcite precipitation. Pressure pulses, vibration and acoustic waves can assist with agitation and distribution. Providing a large surface area for bacterial colonization (e.g., using porous materials) enhances the efficiency of MICP by increasing the sites available for calcite precipitation. Providing nutrients in a periodic or continuous manner rather than in a single dose can sustain bacterial activity and maintain optimal conditions for calcite precipitation over a longer period.

The following is an exemplary mixture ratio:

Urea: 0.5 M

Calcium Chloride: 0.5 M

Ammonium Chloride: 0.17 M

Sodium Bicarbonate: 0.1 M

Yeast Extract/Peptone: 0.1% to 1%

Bacterial Inoculum: $OD_{600}$ of 1.0 to 2.0, mixed in a 1:10 ratio with the nutrient solution The mixture will be in an underwater environment with a pressure at 150 feet of about 550 kPa. Fracturing operations in limestone use a 1,000 to 2,500 psi (approximately 7 to 17 MPa) for hydraulic fracturing operations. In this application, fracturing is not desired so that the mixture spreads or moves outward from the point of injection under pressure and time to the desired radius. In the example, the viscosity of the mixture is similar to water: 1-2 cP with a Ph between 7.5 and 9.0. In the example, initial precipitation and bacteria colonization takes 1 to 3 days and substantial precipitation and void sealing takes about 1 to 2 weeks. Under certain conditions, complete sealing and strengthening takes an additional 2 to 4 weeks or more, and perhaps up to a year or more. However, the barrier can be functional and effective prior.

If additional $CO_2$ is needed during the sealing process, micro-balloons filled with $CO_2$ can be included in the mixture. The balloons dissolve over time and release $CO_2$ (and nutrient) to feed/accelerate the process. Additionally, if a crack exists, balloons burst with the cracking, $CO_2$ leaks out and starts the process of limestone formation again.

Thus, to create an impermeable material, bacteria and nutrients are injected into the voids and fractures within the limestone. This is followed by $CO_2$ enrichment by injecting $CO_2$ to increase carbonate concentration, which aids in more efficient calcite precipitation. After time the bacteria produce urease, hydrolyze urea, and precipitate calcite, filling the voids and forming a solid, impermeable matrix.

An exemplary method of forming a barrier with the material starts with pretreating the limestone by flushing the hole, pores and voids with $CO_2$ to create a favorable environment for bacterial growth. This is followed by injecting the sealing material (*S. pasteurii*, water, and salt) under pressure with $CO_2$. Pressurized injection offers advantages in terms of uniform distribution, continuous delivery, high injection rates, and reduced risk of clogging the injection apparatus and the apertures compared to pulse injection. However, pulse injection does offer precise control and can be used. Salt water may be used or a combination of it and ground water, if necessary. In either case, calcium and sodium chloride can provide nutrients and accelerate the MICP process. Then, $CO_2$ can be applied periodically to support MICP and check for bacterial growth. After time, the MICP process has stabilized, and all pores and voids are filled. Periodic review ensures that bacterial growth is contained.

Thus, to summarize, Microbially Induced Calcite Precipitation (MICP) uses bacteria to help form calcium carbonate, which can fill gaps in limestone, making it impermeable. Bacteria break down urea into ammonium and carbonate and the carbonate reacts with calcium ions to form calcium carbonate. Adding $CO_2$ helps make more carbonate ions available, aiding in calcium carbonate formation. Bacteria (*Sporosarcina pasteurii*) and nutrients (salts) are injected into limestone gaps. $CO_2$ is added to increase carbonate concentration for better calcium carbonate formation. Over time the bacteria causes calcium carbonate to form, filling the voids and gaps. Viscosity is controlled by adjusting salt type and amount to help the solution flow better into limestone. Salt can be used to foster bacterial action. Exemplary salts include calcium chloride, magnesium, or sodium chloride. Calcium and sodium chloride work well together. $CO_2$ is infused into the holes and the sealing material (*S. pasteurii*, water, salt) is injected under pressure with $CO_2$ that can be applied regularly to help the MICP process and monitor bacteria growth. After 2-4 weeks or more, all gaps should be filled.

It will be appreciated by persons skilled in the art that the present invention is not limited to what has been particularly shown and described herein above. In addition, unless mention was made above to the contrary, it should be noted that all the accompanying drawings are not to scale. A variety of modifications and variations are possible in light of the above teachings without departing from the scope and spirit of the invention, which is limited only by the following claims.

What is claimed is:

1. A method of creating a water barrier, comprising:
   providing a mixture that includes bacteria, water, and a calcium source capable of forming a solid material to fill voids in a water permeable subsoil; and
   introducing the mixture into the water permeable subsoil to fill voids, wherein the introduction includes creating a passage in the subsoil and delivering the mixture under pressure.

2. The method of claim 1, wherein the step of introducing includes creating a passage through the water permeable subsoil layer by drilling or inserting an injection pipe and pumping the mixture into the passage.

3. The method of claim 2, wherein the step of introducing includes injecting the mixture into the passage under supplemental pressure provided by a pressurized gas.

4. The method of claim 3, wherein pressurized gas includes pressurized $CO_2$ used to apply supplemental pressure to the mixture.

5. The method of claim 3, wherein the mixture under pressure infiltrates the water permeable subsoil outwardly from the passage.

6. The method of claim 5, wherein the mixture under pressure moves outwardly from the passage to a distance of more than three feet.

7. The method of claim 1, wherein the mixture includes bacteria that react with $CO_2$ to form limestone to fill voids in the water permeable subsoil.

8. The method of claim 1, wherein the mixture includes bacteria that react with $O_2$ and form limestone to fill voids in the water permeable subsoil.

9. The mixture of claim 1, wherein the mixture includes a polymer to enhance the structural integrity of the formed water barrier.

10. The method of claim 1, wherein the mixture includes water and bentonite.

11. The method of claim 1, wherein the mixture includes *Sporosarcina pasteurii* as the bacteria component.

12. The method of claim 1, wherein the mixture includes a material with hydrogel properties to enhance void-filling capabilities.

13. The method of claim 1, further comprising introducing an acid into the water permeable subsoil prior to introducing the mixture to modify the subsoil voids.

14. The method of claim 1, including forming a cap above the barrier that serves as a supplemental water barrier.

15. The method of claim 1, including disposing a heat exchanger within the water barrier to enable geothermal heating or cooling.

16. The method of claim 1, including testing subsoil characteristics and density to determine optimal water barrier placement and mixture formulation.

17. The method of claim 1, including use of one of sonar testing, seismic testing, pulse vibration testing, and core drilling to evaluate the water barrier.

18. The method of claim 1, including forming a plurality of adjacent water barriers to protect a designated area.

19. The method of claim 18, wherein the plurality of adjacent water barriers is disposed between a body of water and an inland area.

20. The method of claim 18, wherein the plurality of adjacent water barriers encircle one or more buildings.

21. The method of claim 7, further comprising infusing the subsoil with $CO_2$ and bacterial nutrients to accelerate limestone formation.

22. The method of claim 1, wherein the mixture includes micro-balloons filed with $CO_2$ that dissolve over time to release $CO_2$ into the subsoil.

* * * * *